(12) United States Patent
Wang et al.

(10) Patent No.: US 8,384,755 B2
(45) Date of Patent: Feb. 26, 2013

(54) PORTABLE REMOTE PRESENCE ROBOT

(75) Inventors: Yulun Wang, Goleta, CA (US); Charles S. Jordan, Santa Barbara, CA (US); Marco Pinter, Santa Barbara, CA (US); Daniel Steven Sanchez, Summerland, CA (US); Kevin Hanrahan, Santa Barbara, CA (US)

(73) Assignee: Intouch Technologies, Inc., Goleta, CA (US)

( * ) Notice: Subject to any disclaimer, the term of this patent is extended or adjusted under 35 U.S.C. 154(b) by 525 days.

(21) Appl. No.: 12/548,122

(22) Filed: Aug. 26, 2009

(65) Prior Publication Data

US 2011/0050841 A1    Mar. 3, 2011

(51) Int. Cl.
*H04N 7/14* (2006.01)

(52) U.S. Cl. .................. 348/14.05; 348/14.07

(58) Field of Classification Search .... 348/14.01–14.09, 348/14.1, 14.11, 14.12; 709/203, 204; 700/13, 700/90, 245; 901/14, 19, 46
See application file for complete search history.

(56) References Cited

U.S. PATENT DOCUMENTS

| | | | |
|---|---|---|---|
| 4,413,693 A | 11/1983 | Derby | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,697,472 A | 10/1987 | Hiyane | |
| 4,709,265 A | 11/1987 | Silverman et al. | |
| 4,751,658 A | 6/1988 | Kadonoff et al. | |
| 4,766,581 A | 8/1988 | Korn et al. | |
| 4,777,416 A | 10/1988 | George, II et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane, III et al. | |

(Continued)

FOREIGN PATENT DOCUMENTS

| | | |
|---|---|---|
| CA | 2289697 | 11/1998 |
| CN | 1554193 A | 12/2004 |

(Continued)

OTHER PUBLICATIONS

Al-Kassab, "A Review of Telemedicine", Journal of Telemedicine and Telecare, 1999, vol. 5, Supplement 1.

(Continued)

*Primary Examiner* — Tuan Nguyen
(74) *Attorney, Agent, or Firm* — Paul Evans

(57) ABSTRACT

A tele-presence system that includes a portable robot face coupled to a remote station. The robot face includes a robot monitor, a robot camera, a robot speaker and a robot microphone. The remote station includes a station monitor, a station camera, a station speaker and a station microphone. The portable robot face can be attached to a platform mounted to the ceiling of an ambulance. The portable robot face can be used by a physician at the remote station to provide remote medical consultation. When the patient is moved from the ambulance the portable robot face can be detached from the platform and moved with the patient.

10 Claims, 5 Drawing Sheets

U.S. PATENT DOCUMENTS

| | | |
|---|---|---|
| 5,006,988 A | 4/1991 | Borenstein et al. |
| 5,040,116 A | 8/1991 | Evans et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,193,143 A | 3/1993 | Kaemmerer et al. |
| 5,217,453 A | 6/1993 | Wilk |
| 5,224,157 A | 6/1993 | Yamada et al. |
| 5,231,693 A | 7/1993 | Backes et al. |
| 5,236,432 A | 8/1993 | Matsen, II et al. |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,350,033 A | 9/1994 | Kraft |
| 5,366,896 A | 11/1994 | Margrey et al. |
| 5,374,879 A | 12/1994 | Pin et al. |
| 5,417,210 A | 5/1995 | Funda et al. |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,682,199 A | 10/1997 | Lankford |
| 5,684,695 A | 11/1997 | Bauer |
| 5,701,904 A | 12/1997 | Simmons et al. |
| 5,739,657 A | 4/1998 | Takayama et al. |
| 5,749,058 A | 5/1998 | Hashimoto |
| 5,749,362 A | 5/1998 | Funda et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,802,494 A | 9/1998 | Kuno |
| 5,836,872 A | 11/1998 | Kenet et al. |
| 5,867,653 A | 2/1999 | Aras et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,966,130 A | 10/1999 | Benman, Jr. |
| 5,973,724 A | 10/1999 | Riddle |
| 5,974,446 A | 10/1999 | Sonnenreich et al. |
| 5,999,977 A | 12/1999 | Riddle |
| 6,133,944 A | 10/2000 | Braun et al. |
| 6,135,228 A | 10/2000 | Asada et al. |
| 6,148,100 A | 11/2000 | Anderson et al. |
| 6,170,929 B1 | 1/2001 | Wilson et al. |
| 6,175,779 B1 | 1/2001 | Barrett |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,321,137 B1 | 11/2001 | De Smet |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,452,915 B1 | 9/2002 | Jorgensen |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,580,246 B2 | 6/2003 | Jacobs |
| 6,584,376 B1 | 6/2003 | Van |
| 6,604,019 B2 | 8/2003 | Ahlin et al. |
| 6,604,021 B2 | 8/2003 | Imai et al. |
| 6,611,120 B2 | 8/2003 | Song et al. |
| 6,646,677 B2 | 11/2003 | Noro et al. |
| 6,650,748 B1 | 11/2003 | Edwards et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,958,706 B2 | 10/2005 | Chaco et al. |
| 6,965,394 B2 | 11/2005 | Gutta et al. |
| 6,995,664 B1 | 2/2006 | Darling |

| Patent/Publication | Date | Inventor |
|---|---|---|
| 7,030,757 B2 | 4/2006 | Matsuhira et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,171,286 B2 | 1/2007 | Wang et al. |
| 7,174,238 B1 | 2/2007 | Zweig |
| 7,184,559 B2 | 2/2007 | Jouppi |
| 7,188,000 B2 | 3/2007 | Chiappetta et al. |
| 7,206,627 B2 | 4/2007 | Abovitz et al. |
| 7,215,786 B2 | 5/2007 | Nakadai |
| 7,256,708 B2 | 8/2007 | Rosenfeld |
| 7,262,573 B2 | 8/2007 | Wang et al. |
| 7,289,883 B2 | 10/2007 | Wang et al. |
| 7,321,807 B2 | 1/2008 | Laski |
| 7,382,399 B1 | 6/2008 | McCall |
| 7,432,949 B2 | 10/2008 | Remy et al. |
| 7,441,953 B2 | 10/2008 | Banks |
| 7,624,166 B2 | 11/2009 | Foote et al. |
| 7,831,575 B2 | 11/2010 | Trossell et al. |
| 7,924,323 B2 | 4/2011 | Walker et al. |
| 7,982,763 B2 | 7/2011 | King |
| 2001/0002448 A1 | 5/2001 | Wilson et al. |
| 2001/0010053 A1 | 7/2001 | Ben-Shachar et al. |
| 2001/0034475 A1 | 10/2001 | Flach et al. |
| 2001/0037163 A1 | 11/2001 | Allard |
| 2001/0051881 A1 | 12/2001 | Filler |
| 2001/0054071 A1 | 12/2001 | Loeb |
| 2002/0015296 A1 | 2/2002 | Howell |
| 2002/0027597 A1 | 3/2002 | Sachau |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0095238 A1 | 7/2002 | Ahlin et al. |
| 2002/0098879 A1 | 7/2002 | Rheey |
| 2002/0104094 A1 | 8/2002 | Alexander et al. |
| 2002/0111988 A1 | 8/2002 | Sato |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0030397 A1 | 2/2003 | Simmons |
| 2003/0048481 A1 | 3/2003 | Kobayashi |
| 2003/0050733 A1 | 3/2003 | Wang et al. |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0100892 A1 | 5/2003 | Morley et al. |
| 2003/0104806 A1 | 6/2003 | Ruef et al. |
| 2003/0114962 A1 | 6/2003 | Niemeyer |
| 2003/0126361 A1 | 7/2003 | Slater et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0199000 A1 | 10/2003 | Valkirs et al. |
| 2003/0206242 A1 | 11/2003 | Choi |
| 2003/0216834 A1 | 11/2003 | Allard |
| 2003/0220541 A1 | 11/2003 | Salisbury et al. |
| 2003/0220715 A1 | 11/2003 | William et al. |
| 2003/0231244 A1 | 12/2003 | Bonilla et al. |
| 2003/0232649 A1 | 12/2003 | Gizis |
| 2004/0012362 A1 | 1/2004 | Tsurumi |
| 2004/0013295 A1 | 1/2004 | Sabe et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0093409 A1 | 5/2004 | Thompson et al. |
| 2004/0098167 A1 | 5/2004 | Yi et al. |
| 2004/0102167 A1 | 5/2004 | Shim et al. |
| 2004/0117065 A1 | 6/2004 | Wang et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0172301 A1 | 9/2004 | Mihai et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0201602 A1 | 10/2004 | Mody et al. |
| 2004/0215490 A1 | 10/2004 | Duchon et al. |
| 2004/0224676 A1 | 11/2004 | Iseki |
| 2004/0230340 A1 | 11/2004 | Fukuchi et al. |
| 2005/0003330 A1 | 1/2005 | Asgarinejad |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0052527 A1 | 3/2005 | Remy et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0099493 A1 | 5/2005 | Chew |
| 2005/0110867 A1 | 5/2005 | Schultz |
| 2005/0154265 A1 | 7/2005 | Miro et al. |
| 2005/0182322 A1 | 8/2005 | Grispo |
| 2005/0192721 A1 | 9/2005 | Jouppi |
| 2005/0204438 A1 | 9/2005 | Wang et al. |
| 2005/0219356 A1 | 10/2005 | Smith et al. |
| 2005/0267826 A1 | 12/2005 | Levy et al. |
| 2005/0283414 A1 | 12/2005 | Fernandes et al. |
| 2006/0007943 A1 | 1/2006 | Fellman |
| 2006/0013263 A1 | 1/2006 | Fellman |
| 2006/0013469 A1 | 1/2006 | Wang et al. |
| 2006/0013488 A1 | 1/2006 | Inoue |
| 2006/0029065 A1 | 2/2006 | Fellman |
| 2006/0047365 A1 | 3/2006 | Ghodoussi et al. |
| 2006/0052676 A1 | 3/2006 | Wang et al. |
| 2006/0052684 A1 | 3/2006 | Takahashi et al. |
| 2006/0064212 A1 | 3/2006 | Thorne |
| 2006/0074525 A1 | 4/2006 | Close et al. |

| | | | | | | |
|---|---|---|---|---|---|---|
| 2006/0082642 A1* | 4/2006 | Wang et al. ............... 348/14.05 | EP | 1536660 A3 | 9/2004 |
| 2006/0087746 A1 | 4/2006 | Lipow | EP | 1536660 A2 | 6/2005 |
| 2006/0095158 A1 | 5/2006 | Lee et al. | EP | 1573406 A2 | 9/2005 |
| 2006/0095170 A1 | 5/2006 | Yang et al. | EP | 1791464 A2 | 6/2007 |
| 2006/0098573 A1 | 5/2006 | Beer et al. | EP | 1800476 A2 | 6/2007 |
| 2006/0103659 A1 | 5/2006 | Karandikar et al. | EP | 1856644 A2 | 11/2007 |
| 2006/0104279 A1 | 5/2006 | Fellman et al. | EP | 1928310 A2 | 6/2008 |
| 2006/0106493 A1 | 5/2006 | Niemeyer et al. | EP | 2027716 A2 | 2/2009 |
| 2006/0122482 A1 | 6/2006 | Mariotti et al. | EP | 2145274 A1 | 1/2010 |
| 2006/0142983 A1 | 6/2006 | Sorensen | EP | 2214111 A2 | 8/2010 |
| 2006/0161303 A1 | 7/2006 | Wang et al. | EP | 2263158 | 12/2010 |
| 2006/0164546 A1 | 7/2006 | Adachi | EP | 2300930 | 3/2011 |
| 2006/0173712 A1 | 8/2006 | Joubert | JP | 07213753 A | 8/1995 |
| 2006/0178776 A1 | 8/2006 | Feingold et al. | JP | 07248823 A | 9/1995 |
| 2006/0189393 A1 | 8/2006 | Edery | JP | 07257422 A | 10/1995 |
| 2006/0195569 A1 | 8/2006 | Barker | JP | 08084328 A | 3/1996 |
| 2006/0259193 A1 | 11/2006 | Wang et al. | JP | 8320727 | 12/1996 |
| 2006/0293788 A1 | 12/2006 | Pogodin | JP | 09267276 A | 10/1997 |
| 2007/0021871 A1 | 1/2007 | Wang et al. | JP | 10079097 | 3/1998 |
| 2007/0046237 A1 | 3/2007 | Lakshmanan et al. | JP | 10288689 | 10/1998 |
| 2007/0064092 A1* | 3/2007 | Sandbeg et al. ............ 348/14.02 | JP | 00032319 A | 1/2000 |
| 2007/0078566 A1 | 4/2007 | Wang et al. | JP | 2000049800 | 2/2000 |
| 2007/0112700 A1 | 5/2007 | Den et al. | JP | 2000079587 | 3/2000 |
| 2007/0117516 A1 | 5/2007 | Saidi et al. | JP | 2000196876 | 7/2000 |
| 2007/0120965 A1 | 5/2007 | Sandberg et al. | JP | 00188124 A | 4/2001 |
| 2007/0135967 A1 | 6/2007 | Jung et al. | JP | 01147718 A | 5/2001 |
| 2007/0142964 A1 | 6/2007 | Abramson | JP | 2001125641 | 5/2001 |
| 2007/0176060 A1 | 8/2007 | White et al. | JP | 01198865 A | 7/2001 |
| 2007/0192910 A1 | 8/2007 | Vu et al. | JP | 01198868 A | 7/2001 |
| 2007/0197896 A1 | 8/2007 | Moll et al. | JP | 01199356 A | 7/2001 |
| 2007/0198128 A1 | 8/2007 | Ziegler et al. | JP | 2001179663 | 7/2001 |
| 2007/0199108 A1 | 8/2007 | Angle et al. | JP | 02000574 A | 1/2002 |
| 2007/0250212 A1 | 10/2007 | Halloran et al. | JP | 00235423 A | 2/2002 |
| 2007/0262884 A1 | 11/2007 | Goncalves et al. | JP | 02046088 A | 2/2002 |
| 2007/0273751 A1 | 11/2007 | Sachau | JP | 02305743 A | 10/2002 |
| 2007/0291109 A1 | 12/2007 | Wang et al. | JP | 02355779 A | 12/2002 |
| 2007/0291128 A1 | 12/2007 | Wang et al. | JP | 2004524824 T | 8/2004 |
| 2008/0011904 A1 | 1/2008 | Cepollina et al. | JP | 2004261941 | 9/2004 |
| 2008/0065268 A1 | 3/2008 | Wang et al. | JP | 2005028066 | 2/2005 |
| 2008/0082211 A1 | 4/2008 | Wang et al. | JP | 20050028066 | 2/2005 |
| 2008/0201017 A1 | 8/2008 | Wang et al. | JP | 2010064154 A | 3/2010 |
| 2008/0215987 A1 | 9/2008 | Alexander et al. | JP | 2010532109 A | 9/2010 |
| 2008/0229531 A1 | 9/2008 | Takida | JP | 246954 A | 11/2010 |
| 2008/0255703 A1 | 10/2008 | Wang et al. | KR | 2006037979 A | 5/2006 |
| 2008/0281467 A1 | 11/2008 | Pinter | KR | 0019479 A | 2/2010 |
| 2009/0055023 A1 | 2/2009 | Walters et al. | KR | 0139037 | 12/2010 |
| 2009/0105882 A1 | 4/2009 | Wang et al. | WO | 93/06690 A1 | 4/1993 |
| 2009/0125147 A1 | 5/2009 | Wang et al. | WO | 98/51078 A1 | 11/1998 |
| 2009/0240371 A1 | 9/2009 | Wang et al. | WO | 99/67067 A1 | 12/1999 |
| 2009/0259339 A1 | 10/2009 | Wright et al. | WO | 0033726 | 6/2000 |
| 2010/0010672 A1 | 1/2010 | Wang et al. | WO | 03/77745 A1 | 9/2003 |
| 2010/0010673 A1 | 1/2010 | Wang et al. | WO | 2004008738 A1 | 1/2004 |
| 2010/0019715 A1 | 1/2010 | Roe et al. | WO | 2004075456 A2 | 9/2004 |
| 2010/0070079 A1 | 3/2010 | Mangaser et al. | WO | 2007041295 A1 | 4/2007 |
| 2010/0073490 A1 | 3/2010 | Wang et al. | WO | 2010003666 A1 | 3/2010 |
| 2010/0115418 A1 | 5/2010 | Wang et al. | WO | 2010120407 A1 | 10/2010 |
| 2010/0131103 A1 | 5/2010 | Herzog et al. | WO | 2011097130 A2 | 8/2011 |
| 2010/1730894 | 6/2010 | Pinter et al. | WO | 2011097132 A2 | 8/2011 |
| 2010/0191375 A1 | 7/2010 | Wright et al. | WO | 2011109336 A2 | 9/2011 |
| 2010/0268383 A1 | 10/2010 | Wang et al. | WO | 2011149902 A2 | 12/2011 |
| 2011/0050841 A1 | 3/2011 | Wang et al. | | | |
| 2011/0071702 A1 | 3/2011 | Wang et al. | | | |
| 2011/0187875 A1 | 8/2011 | Sanchez et al. | | | |
| 2011/0190930 A1 | 8/2011 | Hanrahan et al. | | | |
| 2011/0213210 A1 | 9/2011 | Temby et al. | | | |
| 2011/0218674 A1 | 9/2011 | Stuart et al. | | | |
| 2011/0292193 A1 | 12/2011 | Wany et al. | | | |
| 2011/0301759 A1 | 12/2011 | Wang et al. | | | |

FOREIGN PATENT DOCUMENTS

| | | |
|---|---|---|
| CN | 1554985 A | 12/2004 |
| CN | 101106939 A | 1/2008 |
| CN | 101390098 A | 3/2009 |
| CN | 101507260 A | 8/2009 |
| CN | 1866396 A | 10/2010 |
| EP | 0466492 | 1/1992 |
| EP | 0488673 A2 | 6/1992 |
| EP | 0981905 B1 | 1/2002 |
| EP | 1262142 A2 | 12/2002 |

OTHER PUBLICATIONS

Fiorini, "Health Care Robotics: A Progress Report", IEEE International Conference on Robotics and Automation, pp. 1271-1276, Apr. 1997.

Murphy, "Introduction to AI Robotics", 2000.

Fiorini, P. et al., "Health Care Robotics: A Progress Report", IEEE International Conference on Robotics and Automation, 1997.

Goldenberg, et al., "Telemedicine in Otolaryngology", American Journal of Otolaryngology vol. 23, No. 1, 2002, 35-43.

Hameed, et al., "A Review of Telemedicine", Journal of Telemedicine and Telecare, vol. 5, Supplement 1, 1999.

Han, et al., "Construction of an Omnidirectional Mobile Robot Platform Based on Active Dual-Wheel Caster Mechanisms and Development of a Control Simulator", Kluwer Academic Publishers, vol. 29, Nov. 2000, 257-275.

Tahboub, Karim A. et al., "Dynamics Analysis and Control of a Holonomic Vehicle With Continously Variable Transmission", Journal of Dynamic Systems, Measurement and Control ASME vol. 124, Mar. 2002, pp. 118-126.

Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.

"Defendant VGo Communications, Inc.'s Invalidity Contentions Pursuant to the Feb. 27, 2012 Civil Minute Order", May 2, 2012, pp. 1-143.

"Defendant-Counterclaimant VGo Communications, Inc.'s Supplemental Invalidity Contentions Pursuant to the Feb. 27, 2012 Civil Minute Order", May 14, 2012, pp. 1-228.

Dudenhoeffer, et al., "Command and Control Architectures for Autonomous Micro-Robotic Forces", http://www.inl.gov/technicalpublications/Documents/3157051.pdf, Apr. 2001.

Elhajj, "Real-Time Haptic Feedback in Internet-Based Telerobotic Operation", EEE International Conference on Electro/Information Technology, http://www.egr.msu.edu/~ralab-web/cgi_bin/internet-teleoperation.php, Jun. 2000.

Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.

ITU, "ITU-T H.281 A Far End Camera Control Protocol for Videoconferences using H.224", http://www.itu.int/rec/T-RECH.281-199411-I/en, Nov. 1994.

ITU, "ITU-T H.450.11 Call Intrusion Supplementary Service for H.323", http://www.itu.int/rec/T-RECH.450.11-200103-I/en, Mar. 2001.

ITU, "ITU-T H.450.9 Call Completion Supplementary Services for H.323", http://www.itu.int/rec/T-RECH.450.9-200011-I/en, Nov. 2000.

Metz, "HP Labs", PCMAG.com, http://www.pcmag.com/article2/0,2817,1130820,00.asp, Jul. 1, 2003.

Picturetel, "PictureTel Live200 for Windows NT Product Guide", http://support.polycom.com/global/documents/support/user/products/video/live200_live200NT_product_guide.pdf, Nov. 1994.

Roach, "Automatic Call Back Service in SIP", http://tools.ietf.org/pdf/draftroach-sip-acb-00.pdf, Mar. 2000.

Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.

Zambroski, "CMU, Pitt Developing 'nursebot'", http://www.cs.cmu.edu/~nursebot/web/press/tribunereview.html, Oct. 27, 2000.

Adams, Chris. "Mobile Robotics Research Group", Mobile Robotics Research Group, Edinburgh University, http://www.dai.ed.ac.uk/groups/mrg/MRG.html, Internet, pp. 1-2, 2000.

Ando, et al., "A Multimedia Self-service Terminal with Conferencing Functions", IEEE, Jul. 5-7, 1995, pp. 357-362.

Android Amusement Corp., "What Marketing Secret . . . Renting Robots from Android Amusement Corp!", (Advertisement), 1982.

Applebome, "Planning Domesticated Robots for Tomorrow's Household", New York Times, http://www.theoldrobots.com/images17/dc17.JPG, Mar. 4, 1982, pp. 21, 23.

Bar-Cohen, et al., "Virtual reality robotic telesurgery simulations using MEMICA haptic system", Internet, Mar. 5, 2001, pp. 1-7.

Bartholomew, "An Apothecary's Pharmacy", http://classes.bnf.fr/ema/grands/034.htm, pp. 1230-1240.

Bauer, Jeffrey C. et al., "Service Robots in Health Care: The Evolution of Mechanical Solutions to Human Resource Problems", Jun. 2003.

Bauer, John et al., "Remote telesurgical mentoring: feasibility and efficacy", IEEE, 2000, pp. 1-9.

Bischoff, "Design Concept and Realization of the Humanoid Service Robot Hermes", Field and Service Robotics, Springer, London, 1998, pp. 485-492.

Blackwell, Gerry, "Video: A Wireless LAN Killer App?", Internet, Apr. 16, 2002, pp. 1-3.

Breslow, Michael J. et al., "Effect of a multiple-site intensive care unit telemedicine program on clinical and economic outcome An alternative paradigm for intensivist staffing", Critical Care Med; vol. 32 No. 1, Jan. 2004, pp. 31-38.

Brooks, Rodney, "Remote Presence", Abstracts from Flesh & Machines, How Robots Will Change Us, Feb. 2002, pp. 131-147.

Candelas, Herias et al., "Flexible virtual and remote laboratory for teaching Robotics", Formatex 2006; Proc. Advance in Control Education Madrid, Spain, Jun. 2006, pp. 21-23.

Celt, et al., "The EICU: Its not just telemedicine", Critical Care Medicine vol. 29, No. 8 (Supplement), Aug. 2001.

Cheetham, Anastasia et al., "Interface Development for a Child's Video Conferencing Robot", 2000, pp. 1-4.

Cleary, et al., "State of the art in surgical robotics: Clinical applications and technology challenges", Internet, Feb. 24, 2002, pp. 1-26.

CNN, "Floating 'droids' to roam space corridors of the future", Internet, Jan. 12, 2000, pp. 1-4.

CNN.com/technology, "Paging R.Robot: Machine helps doctors with patients", Internet, Sep. 30, 2003, 1-3.

Crowley, Susan L., "Hello to Our Future", AARP Bulletin, http://www.cs.cmu.ed/-nursebot/web/press/aarp 99_14/millennium.html, Jan. 2000.

Dalton, "Techniques for Web Telerobotics", PhD Thesis, University of Western Australia, http://telerobot.mech.uwa.edu.au/information.html, http://catalogue.library.uwa.edu.au/search, 2001, 27-62 pp. 149-191.

Davies, "Robotics in Minimally Invasive Surgery", Internet, 1995, pp. 5/1-5/2.

Digiorgio, James, "Is Your Emergency Department of the 'Leading Edge?", Internet, 2005, pp. 1-4.

Discovery Channel Canada, "Inventing the Future: 2000 Years of Discovery", (Video Transcript), Jan. 2, 2000.

Elhajj, et al., "Supermedia in Internet-based telerobotic operations", Internet, 2001, pp. 1-14.

Elhajj, et al., "Synchronization and Control of Supermedia Transmission Via the Internet", Proceedings of 2001 International Symposium on Intelligent Multimedia Video and Speech Processing., Hong Kong, May 2-4, 2001.

Ellison, et al., "Telerounding and Patient Satisfaction Following Surgery", pp. 523-530.

Fels, "Developing a Video-Mediated Communication System for Hospitalized Children", Telemedicine Journal, vol. 5, vol. 5, No. 2, 1999.

Fetterman, "Videoconferencing over the Internet", Internet, 2001, pp. 1-8.

Fiorini, P., et al, "Health Care Robotics: A Progress Report", IEEE International Conference on Robotics and Automation, Apr. 1997, pp. 1271-1276.

Ghiasi, et al., "A Generic Web-based Teleoperations Architecture: Details and Experience", SPIE Conference on Telemanipulator and Telepresence Technologies VI, Sep. 1999.

Goldberg, et al., "Collaborative Teleoperation via the Internet", IEEE International Conference on Robotics and Automation, San Francisco, California, Apr. 2000.

Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszSzraiders.odf/aol, 1995, pp. 654-659.

Goldberg, "More Online Robots, Robots that Manipulate", Internet, Updated Aug. 2001, http://ford.ieor.berkeley.edu/ir/robots_a2.html, Aug. 2001.

Goldman, Lea, "Machine Dreams", Entrepreneurs, Forbes, May 27, 2002.

Gump, Michael D., "Robot Technology Improves VA Pharmacies", Internet, 2001, pp. 1-3.

Handley, et al., "RFC 2327—SDP:Session Description Protocol", http://www.faqs.org/rfcs/rfc2327.html, Apr. 1998.

Hanebeck, et al., "Roman: A mobile Robotic Assistant for Indoor Service Applications", Proceedings of the 1997 IEEE/RSJ International Conference on Intelligent Robots and Systems, 1997.

Harmo, et al., "Moving Eye-Interactive Telepresence Over Internet With a Ball Shaped Mobile Robot", 2000.

Haule, et al., "Control Scheme for Delayed Teleoperation Tasks", Proceedings of the Pacific Rim Conference on Communications, Computer and Signal Processing, May 17, 1995.

Hees, William P., "Communications Design for a Remote Presence Robot", Jan. 14, 2002.

Holmberg, "Development of a Holonomic Mobile Robot for Mobile Manipulation Tasks", International Conference on Field and Service Robotics, Pittsburgh, PA, Aug. 1999.

Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.

Ishihara, et al., "Intelligent Microrobot DDS (Drug Delivery System) Measured and Controlled by Ultrasonics", IEEE/RSJ, vol. 2, Nov. 3-5, 1991, pp. 1145-115.

ITU, "ITU-T H.323 Packet-based multimedia communications", http://www.itu.int/rec/T-REC-H.323-199802-S/en, Feb. 1998.

Ivanova, Natali, "Master's thesis: Internet Based Interface for Control of a Mobile Robot", Department of Numerical Analysis and Computer Science, 2003, 59 pages.

Jenkins, et al., "Telehealth Advancing Nursing Practice", Nursing Outlook, vol. 49, No. 2, Mar./Apr. 2001.

Johanson, "Supporting video-mediated communication over the Internet", Chalmers University of Technology,Dept of Computer Engineering, Gothenburg, Sweden, 2003.

Jouppi, et al., "Mutually-Immersive Audio Telepresence", Audio Engineering Society Convention Paper presented at 113th Convention, Oct. 2002.

Jouppi, Norman et al., "First Steps Towards Mutually-Immersive Mobile Telepresence", CSCW, 02, New Orleans LA, Nov. 16-20, 2002.

Kanehiro, Fumio et al., "Virtual Humanoid Robot Platform to Develop Controllers of Real Humanoid Robots without Porting", IEEE, 2001, pp. 3217-3276.

Kaplan, A. E. et al., "An Internet Accessible Telepresence", {aek keshav nls jhv}@research.att.com, AT&T Bell Laboratories, Murray Hill, N.J., pp. 1-7.

Keller, et al., "Raven Interface Project", http://upclose.lrdc.pitt.edu/people/louw_assets/Raven_Slides.pps, Fall 2001.

Khatib, "Robots in Human Environments", Proc. International Conference on Control, Automation, Robotics, and Vision ICRACV2000, Singapore, Dec. 2000, pp. 454-457.

Kuzuoka, et al., "Can The GestureCam Be A Surrogate?", Proceedings of the Fourth European Conference on Computer-Supported Cooperative Work, Sep. 10-14, pp. 181-196.

Lane, "Automated Aides", Newsday, http://www.cs.cum.edu/nursebot/web/press/nd4380.htm, Oct. 17, 2000.

Lee, et al., "A novel method of surgical instruction: International telementoring", Internet, 1998, pp. 1-4.

Lim, Hun-Ok et al., "Control to Realize Human-like Walking of a Biped Humanoid Robot", IEEE, 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs, 2004.

Loeb, et al., "Virtual Visit: Improving Communication for Those Who Need It Most", Stud Health Technol Inform.; 94: 2003 pp. 302-308.

Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.

Luna, Nancy, "Robot a new face on geriatric care", OC Register, Aug. 6, 2003.

Mack, "Minimally invasive and robotic surgery", Internet IEEE, 2001, pp. 568-572.

Mair, "Telepresence—The Technology. And Its Economic and Social Implications", IEEE Technology and Society, 1997.

Martin, Anya, "Days Ahead", Assisted Living Today, vol. 9, Nov./Dec. 2002, pp. 1922.

McCardle, et al., "The challenge of utilizing new technology in design education", Internet, 2000, pp. 122-127.

Meng, et al., "E-Service Robot in Home Healthcare", Proceedings of the 2000 IEEE/RSJ, International Conference on Intelligent Robots and Systems, 2000, pp. 832-837.

Michaud, "Introducing Nursebot", The Boston Globe, http://www.cs.cmu.edu/nursebot/web/press/globe 3 01/index.html, Sep. 11, 2001, pp. 1-5.

Montemerlo, "Telepresence: Experiments in Next Generation Internet", CMU Robotics Institute, http://www.ri.cmu.edu/creative/archives.htm (Video/Transcript), Oct. 20, 1998.

Murphy, "Introduction to A1 Robotics", A Bradford Book, 2000, p. 487.

Nakajima, et al., "A Multimedia Teleteaching System using an Electronic VVhiteboard for Two Way Communication of Motion Videos and Chalkboards", IEEE, 1993, pp. 436-441.

Nomadic Technologies Inc., "Nomad XR4000 Hardware Manual", Release 1.0, Mar. 1999.

Nt'l Energy Res Sci Comp Ctr, "Berkeley Lab's RAGE Telepresence Robot Captures R&D100 Award", http://www.nersc.gov/news/newsroom/RAGE070202.php, Jul. 2, 2002.

Ogata, et al., "Development of Emotional Communication Robot: WAMOEBA-2r—Experimental evaluation.", IEEE, 2000, pp. 175-180.

Ogata, et al., "Emotional Communication Robot: WAMOEBA-2R—Emotion Model and Evaluation Experiments", Internet, 1999, pp. 1-16.

Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper.pdf, 2000.

Ojha, A. K., "An application of Virtual Reality in Rehabilitation", IEEE, Apr. 10-13, 1994, pp. 4-6.

Paulos, et al., "A World Wide Web Telerobotic Remote Environment Browser", http://vive.cs.berkeley.edu/capek, 1995.

Paulos, "Designing Personal Tele-embodiment", IEEE International Conference on Robotics and Automation http://www.prop.org/papers/icra98.pdf, 1998.

Paulos, "PRoP: Personal Roving Presence", ACM:CHI Proceedings of CHI '98, http://www.prop.org/papers/chi98.pdf, 1998, p. 6.

Paulos, et al., "Ubiquitous Tele-embodiment: Applications and Implications", International Journal of Human Computer Studies, vol. 46, No. 6, Jun. 1997, pp. 861-877.

Paulos, "Video of PRoP 2 at Richmond Field Station", www.prop.org Printout of Home Page of Website and two-page Transcript of the audio portion of said PRoP Video, May 2001.

Pin, et al., "A New Family of Omnidirectional and Holonomic Wheeled Platforms for Mobile Robots", IEEE, vol. 10, No. 4, Aug. 1994.

Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.

Roy, et al., "Towards Personal Service Robots for the Elderly", Internet, Mar. 7, 2002, 7 pgs.

Salemi, et al., "MILO: Personal robot platform", Internet, 2005, pp. 1-6.

Sandt, Frederic et al., "Perceptions for a Transport Robot in Public Environments", IROS, 1997.

Schaeffer, "Care-O-bot: A System for Assisting Elderly or Disabled Persons in Home Environments", Proceedings of AAATE-99, http://morpha.de/download/publications/IPA, 1999.

Schulz, "Web Interfaces for Mobile Robots in Public Places", Robotics & Automation Magazine, IEEE, vol. 7, Issue 1, Mar. 2000.

Shimoga, et al., "Touch and force reflection for telepresence surgery", IEEE, 1994, pp. 1049-1050.

Siegwart, "Interacting Mobile Robots on the Web", Proceedings of the 1999 IEEE International Conference on Robotics and Automation, May 1999.

Simmons, "Xavier: An Autonomous Mobile Robot on the Web", IEEE Robotics and Automation Magazine, 1999, pp. 43-48.

Spawar Systems Center, "Robart", San Diego, CA, http://www.nosc.mil/robots/land/robart/robart.html, 1998, pp. 1-8.

Stephenson, Gary, "Dr. Robot Tested at Hopkins", Internet, Aug. 5, 2003, pp. 1-2.

Stoianovici, et al., "Robotic Tools for Minimally Invasive Urologic Surgery", Internet, Dec. 2002, pp. 1-17.

Suplee, "Mastering the Robot", The Washington Post, http://www.cs.cmu.edu-nursebotlweb/press/wash/index.html, Sep. 17, 2000, p. A01.

Tendick, et al., "Human-Machine Interfaces for Minimally Invasive Surgery", IEEE, 1997, pp. 2771-2776.

Thrun, et al., "Probabilistic Algorithms and the Interactive Museum Tour-Guide Robot Minerva", Internet, 2000, pp. 1-35.

Tzafestas, et al., "VR-based Teleoperation of a Mobile Robotic Assistant: Progress Report", Internet, Nov. 2000, pp. 1-23.

Urquhart, Kim, "InTouch's robotic Companion 'beams up' healthcare experts", Medical Device Daily, vol. 7, No. 39, Feb. 27, 2003, p. 1-4.

Weiss, et al., "Telework and video-mediated communication: Importance of real-time, interactive communication for workers with disabilities", California State University Northridge http://www.csun.edu/edu/cod/conf/1999/proceedings/session0238.html, pp. 1-4.

West, et al., "Design of Ball Wheel Mechanisms for Omnidirectional Vehicles with Full Mobility and Invariant Kinematics", Journal of Mechanical Design, vol. 119, Jun. 1997, pp. 153-161.

Yamasaki, et al., "Applying Personal Robots and Active Interface to Video Conference Systems", Internet, 1995, pp. 243-248.

Yamauchi, "PackBot: A Versatile Platform for Military Robotics", Internet, 2004, pp. 1-10.

Yong, et al., "Robot task execution with telepresence using virtual reality technology", Internet, 1998, pp. 1-8.

Zamrazil, Kristie, "Telemedicine in Texas: Public Policy Concerns", House Research Organization Focus Report, Texas House of Representatives, http://www.hro.house.state.tx.us/focus/telemed.pdf, May 5, 2000, pp. 76-22.

Zipperer, Lorri, "Robotic dispensing system", ISMP Medication Safety Alert! vol. 4, Issue 17, Aug. 25, 1999, pp. 1-2.

Zorn, Benjamin G., "Ubiquitous Telepresence", http://www.cs.colorado.edu/-zom/utlvision/vision.html, May 5, 1996.

Dudenhoeffer, et al., "Command And Control Architectures for Autonomous Micro- Robotic Forces", http://www.inl.gov/technicalpublications/Documents/3157051.pdf, Apr. 2001.

Picturetel, "PictureTel Live200 for Windows NT Product Guide", http://support.polycom.com/global/documents/support/user/products/video/live200_live2OONT_product_guide.pdf, Nov. 1994.

Roach, "Automatic Call Back Service in SIP", http://tools.ietforg/pdf/draftroach-sip-acb-00.pdf, Mar. 2000.

* cited by examiner

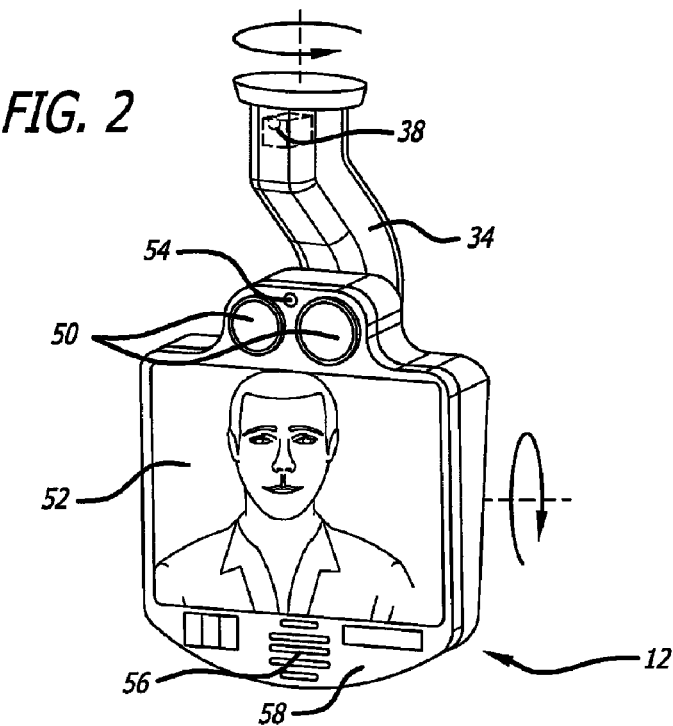
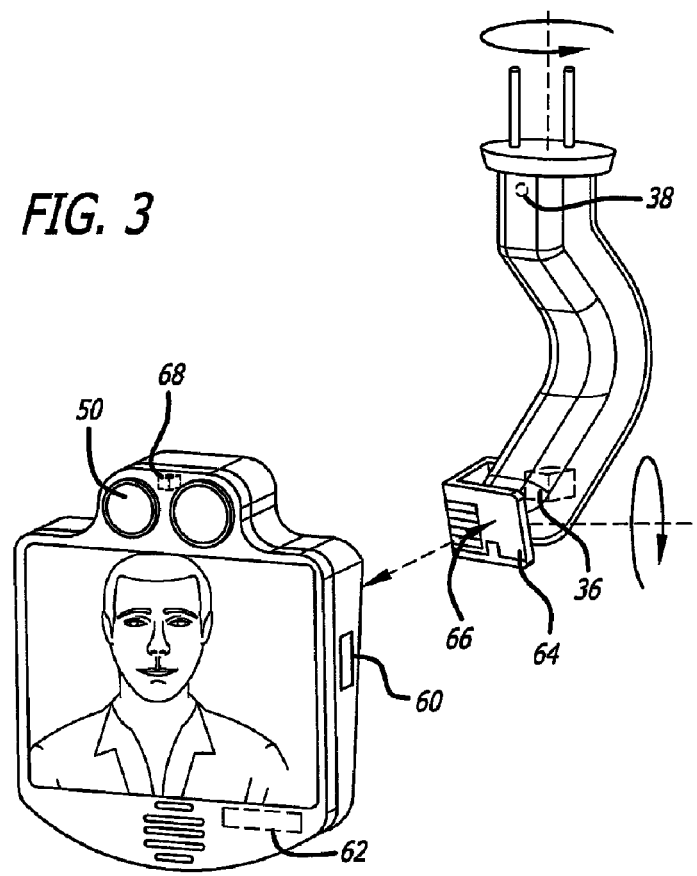

PORTABLE REMOTE PRESENCE ROBOT

BACKGROUND OF THE INVENTION

1. Field of the Invention

The subject matter disclosed generally relates to the field of robotic tele-presence systems.

2. Background Information

Robots have been used in a variety of applications. For example, robots have been used in manufacturing facilities, bomb detection/detonation, medical facilities, etc. The assignee of the present application has developed a tele-presence robot that includes a robot that is remotely controlled through a remote control station. The system is marketed under the product name RP-7. Both the robot and the remote station include cameras, monitors, microphones and speakers to allow for two audio-visual communication. The remote station also includes a joystick that can be operated by the user to move the robot and a robot head.

BRIEF SUMMARY OF THE INVENTION

A tele-presence system that includes a portable robot face coupled to a remote station. The robot face includes a robot monitor, a robot camera, a robot speaker and a robot microphone. The remote station includes a station monitor, a station camera, a station speaker and a station microphone.

BRIEF DESCRIPTION OF THE DRAWINGS

FIG. 2 is an illustration showing the portable robot face within the ambulance;

FIG. 3 is an illustration showing the portable robot face detached from a platform mounted to the ambulance ceiling;

DETAILED DESCRIPTION

Disclosed is a tele-presence system that includes a portable robot face coupled to a remote station. The robot face includes a robot monitor, a robot camera, a robot speaker and a robot microphone. The remote station includes a station monitor, a station camera, a station speaker and a station microphone. The portable robot face can be attached to a platform mounted to the ceiling of an ambulance. The portable robot face can be used by a physician at the remote station to provide remote medical consultation. When the patient is moved from the ambulance the portable robot face can be detached from the platform and moved with the patient.

Figure 1:
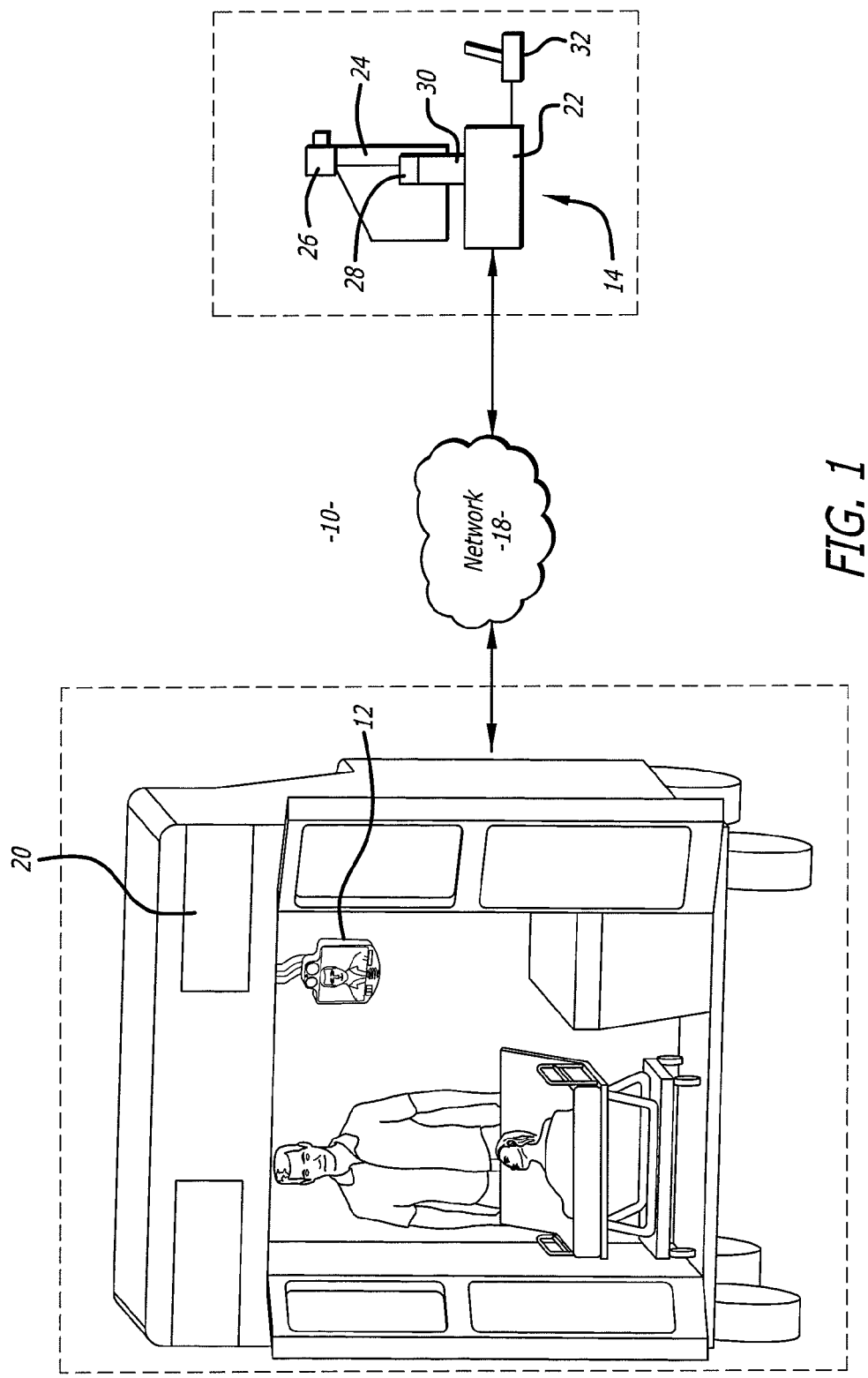
FIG. 1 is an illustration of a tele-presence system that includes a remote station coupled to a portable robot face located within an ambulance.

Referring to the drawings more particularly by reference numbers, FIG. 1 shows a tele-presence system 10. The system 10 includes a portable robot face 12 that is coupled to a remote control station 14 through a wireless network 18. The wireless network may be a cellular broadband network and/or a WiFi network. The portable robot face 12 is located within an ambulance 20.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the robot face 12. Although only one remote control station 14 is shown, the system 10 may include a plurality of remote stations 14. In general any number of robot faces 12 may be coupled to any number of remote stations 14 or other robot faces 12. For example, one remote station 14 may be coupled to a plurality of robot faces 12, or one robot face 12 may be coupled to a plurality of remote stations 14, or a plurality of robot faces 12. The system may include an arbitrator (not shown) that controls access between the robot face(s) 12 and the remote stations 14.

As shown in FIGS. 2 and 3, the portable robot face 12 may be attached to a platform 34. The platform 34 may extend from the ceiling (not shown) of the ambulance 20. The platform 34 may include articulate joints 36 and 38 that provide at least two degrees of freedom and allow a user to move the robot face 12 to different positions to view a patient and an EMT within the ambulance.

Each robot face 12 includes a camera(s) 50, a monitor 52, a microphone(s) 54 and a speaker(s) 56 that are all attached to a housing 58. The robot camera 50 is coupled to the remote monitor 24 so that a user at the remote station 14 can view the patient and/or EMT. Likewise, the robot monitor 52 is coupled to the remote camera 26 so the patient and EMT may view the user of the remote station 14. The microphones 28 and 54, and speakers 30 and 56, allow for audible communication between the system operator and the patient and/or EMT.

The system 10 allows a system user such as a physician to view a patient in the ambulance and provide remote medical consultation through the remote station 14 and the robot face 12. Personnel such as the EMT can transmit questions and responses through the system back to the physician. The robot camera 50 allows the physician to view the patient and enhance the medical consultation. The robot monitor 52 can display the physician to provide a feeling of presence in the ambulance. The platform 34 allows the physician to pan and tilt the robot face 12.

The robot face 12 may include a wireless transceiver 60 that is coupled to the wireless network. The portable face 12 also includes a battery 62.

The system 10 may have certain components and software that are the same or similar to a robotic system provided by the assignee InTouch-Health, Inc. of Santa Barbara, Calif. under the name RP-7 and embodies a system described in U.S. Pat. No. 6,925,357, which is hereby incorporated by reference.

As shown in FIG. 3, the portable robot face 12 can be detached from the platform 34. The robot face 12 and platform 34 may have mechanical connectors 64 that allow the face 12 to be readily attached and detached from the platform 34. Likewise, the robot face 12 and platform 34 may include electrical connectors 66. The ambulance may include a wireless transceiver (not shown) that can provide wireless communication to the remote station. The electrical connectors 66 provide an electrical connection between the robot face 12 and the ambulance wireless transceiver. The connectors 66 may also provide power to the robot face 12. Alternatively, the wireless transceiver 60 of the robot face 12 may be coupled to the remote station through the ambulance wireless transceiver. The robot face may include an actuator system 68 that can move the camera 50 in two degrees of freedom. This allows the operator to move the camera field of view even when the face 12 is detached from the platform 34.

Figure 4:
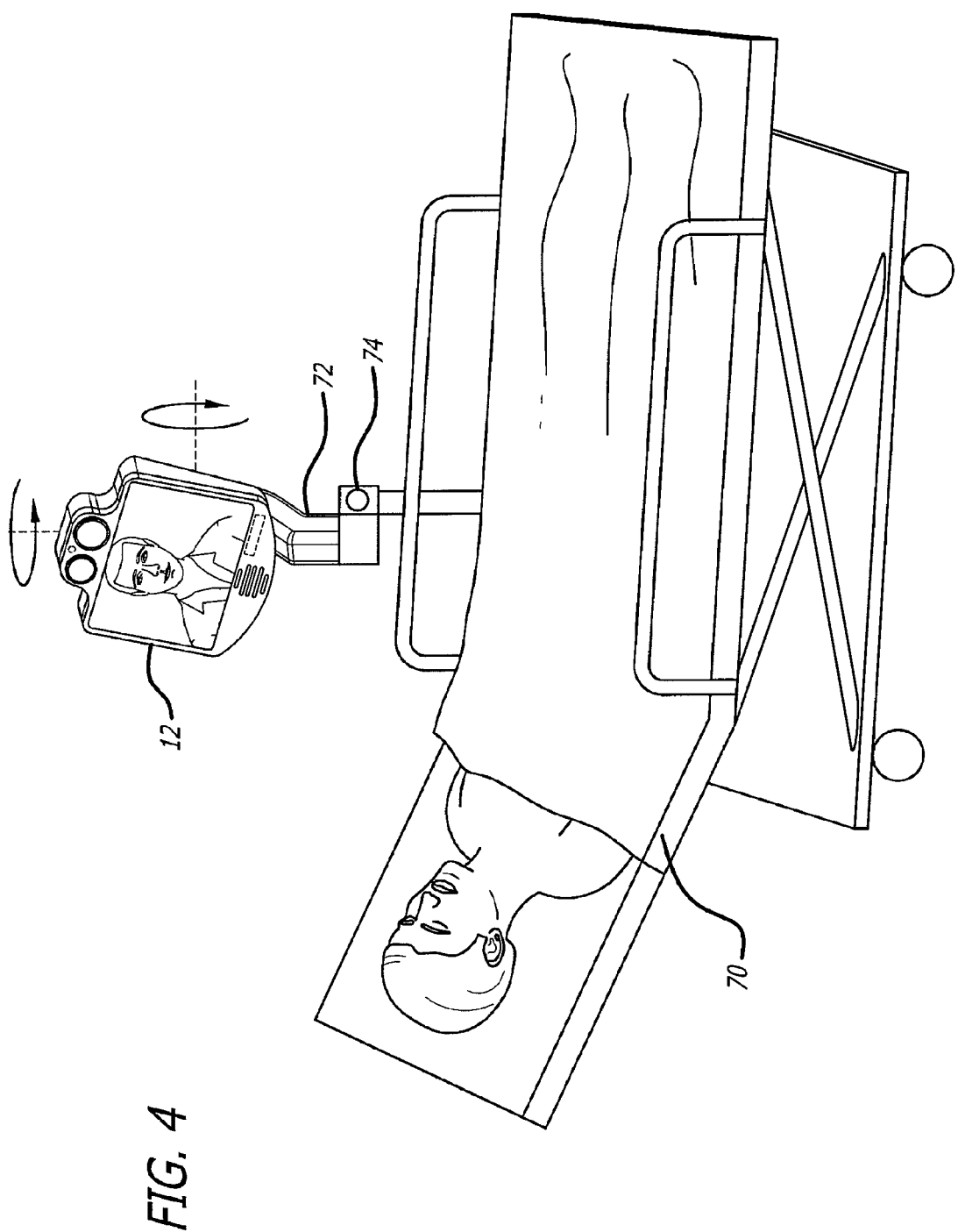
FIG. 4 is an illustration showing the portable robot face attached to a patient gurney.

As shown in FIG. 4 the portable robot face 12 can be detached from the platform (not shown) and attached to the patient gurney 70. The robot face 12 may be attached to a platform 72 with two degrees of freedom that allow the remote station user to move the robot face 12. The platform 72 may include a clamp 74 that allows for attachment to the gurney 70. The robot face 12 and patient can be moved out of the ambulance on the gurney 70. The portable aspect of the robot face 12 allows the face to be moved with the patient. The robot face 12 should be of a size and weight so that an individual can lift the face 12.

Figure 5:
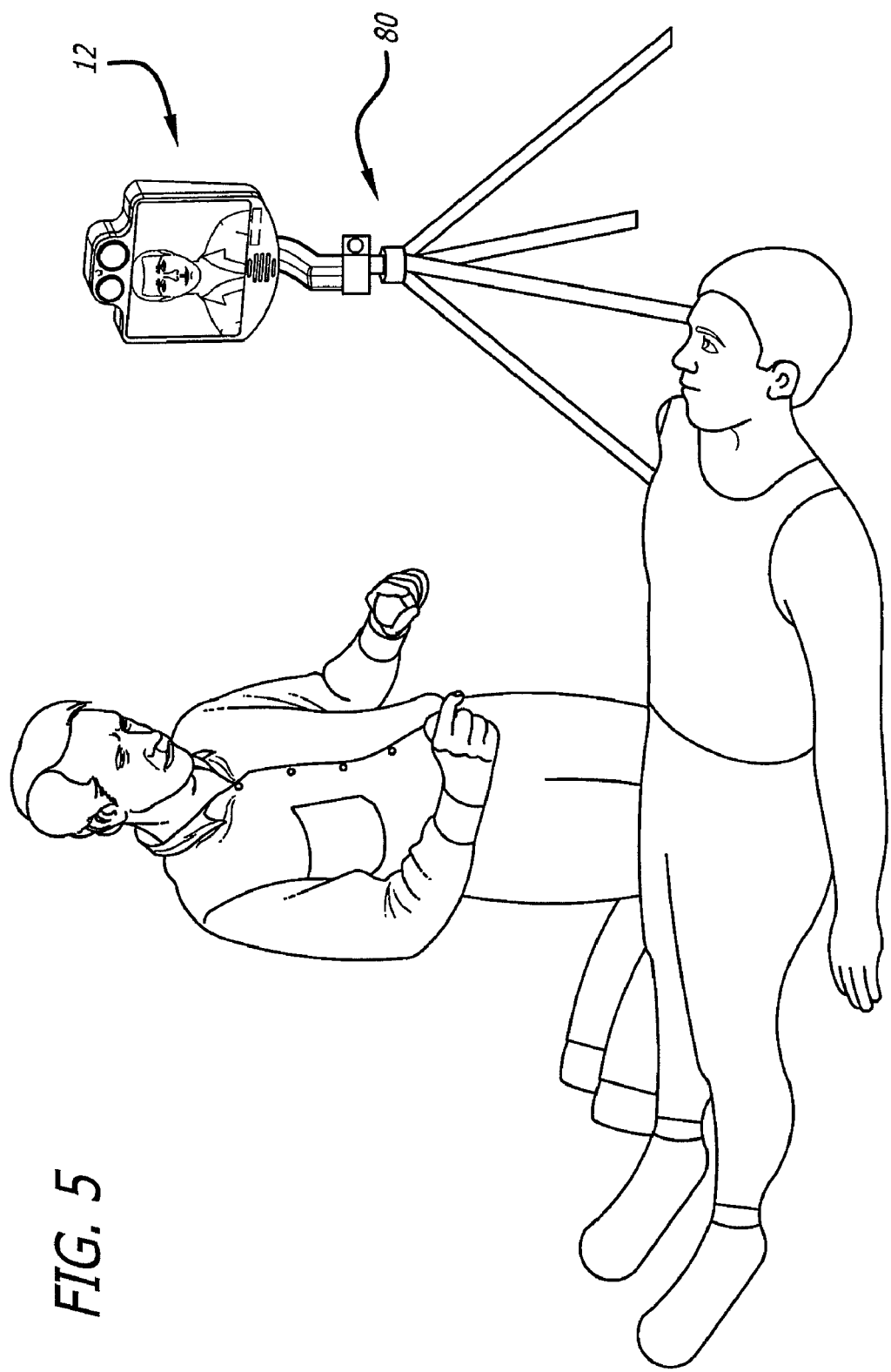
FIG. 5 is an illustration showing the portable robot face attached to a stand.

As shown in FIG. 5 the portable robot face 12 can be detached from the ambulance platform (not shown) and attached to a stand 80 at a remote location. The portable nature of the robot face 12 allows the face 12 to be taken to any location to allow for remote tele-presence of the operator of the remote station. If the operator is a physician the portable robot face 12 allows for remote medical consultation at any site.

Figure 6:
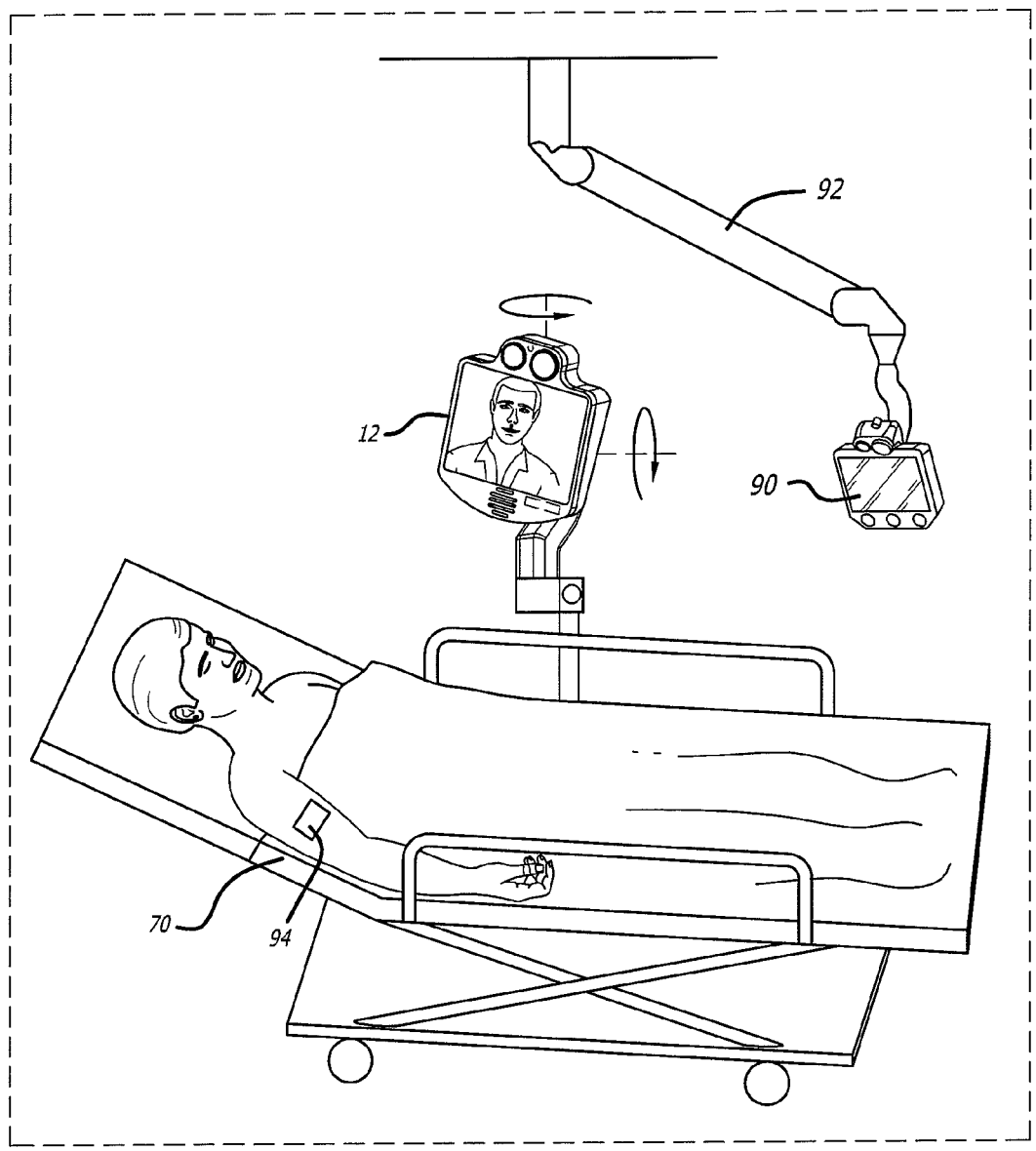
FIG. 6 is an illustration showing a patient within a healthcare facility that has a robot face attached to a boom.

FIG. 6 shows the patient and gurney moved into a healthcare facility with a robot face 90 attached to a boom 92. When the gurney 70 is moved into close proximity with the healthcare facility the robot face wireless transceiver may be coupled to the remote station thru the healthcare facility local wireless network such as a WiFi network. Once inside the facility the portable robot face can be connected to an electrical power outlet and a network for Ethernet connection. An electronic identification (ID) device 94 may be attached to the patient. The ID device 94 may transmit a wireless signal to the robot face 90 attached to the boom 92. Receipt of the signal by the face 90 may cause the remote station to be coupled to the robot face 90 attached to the boom 92 instead of the portable robot face 12. The robot face 90 may be coupled to the remote station by other means. For example, a nurse may type in information into the healthcare facility network system that identifies the new location of the patient. Such an entry may cause the system to switch the remote control station to the robot face 90. Additionally, there may be other methodologies for inducing the system to automatically transfer the remote station from one robot to another robot.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for providing a remote medical consultation, comprising:
capturing an image of a physician with a station camera of a remote station, the remote station includes a station monitor, a station speaker and a station microphone;
transmitting the physician image to a portable robot face mounted to a platform, the robot face including a robot monitor, a robot camera, a robot speaker and a robot microphone;
displaying the physician image on the robot monitor;
capturing an image of a patient with the robot camera;
transmitting the patient image to the remote station;
displaying the patient image on the station monitor of the remote station;
transmitting an audio command from the station microphone to the robot speaker;
detaching the portable robot face from the platform; and,
attaching a wireless identification (ID) device to the patient and moving the patient into a healthcare facility that includes a robot face attached to a boom, the robot face receives a wireless signal from the wireless identification (ID) device and the remote station becomes coupled to the robot face attached to the boom.

2. The method of claim 1, wherein the platform is attached to an ambulance.

3. The method of claim 1, further comprising attaching the portable robot face to a patient gurney.

4. The method of claim 1, further comprising coupling the portable robot face to a healthcare facility network through a wireless transceiver of the portable robot face.

5. A method for providing a remote medical consultation, comprising:
capturing an image of a physician with a station camera of a remote station, the remote station includes a station monitor, a station speaker and a station microphone;
transmitting the physician image to a portable robot face mounted to a platform, the robot face including a robot monitor, a robot camera, a robot speaker and a robot microphone;
displaying the physician image on the robot monitor;
capturing an image of a patient with the robot camera;
transmitting the patient image to the remote station;
displaying the patient image on the station monitor of the remote station;
transmitting an audio command from the station microphone to the robot speaker;
moving the patient into a healthcare facility that includes a robot face attached to a boom, the robot face receives a wireless signal from a wireless identification (ID) device associated with the patient; and,
coupling the robot face of the healthcare facility to the remote station.

6. A method for providing medical consultation, comprising:
capturing an image of a physician with a station camera of a remote station, the remote station includes a station monitor, a station speaker and a station microphone;
transmitting the physician image to a first robot, the first robot includes a robot monitor, a robot camera, a robot speaker and a robot microphone;
displaying the physician image on the robot monitor;
capturing an image of a patient with the robot camera;
transmitting the patient image to the remote station;
displaying the patient image on the station monitor of the remote station;
transmitting an audio command from the station microphone to the robot speaker;
moving the patient into a vicinity of a second robot; and,
coupling automatically the remote station to the second robot, wherein the second robot of the healthcare facility receives a wireless signal from a wireless identification (ID) device associated with the patient that causes the remote station to become coupled to the second robot.

7. A method for providing a remote medical consultation, comprising:
capturing an image of a physician with a station camera of a remote station, the remote station includes a station monitor, a station speaker and a station microphone;
transmitting the physician image to a portable face mounted to an ambulance, the portable face including a face monitor, a face camera, a face speaker and a face microphone;
displaying the physician image on the face monitor;
capturing an image of a patient with the face camera;
transmitting the patient image to the remote station;
displaying the patient image on the station monitor of the remote station;

transmitting an audio command from the station microphone to the face speaker;
detaching the portable face from the ambulance; and,
attaching a wireless identification (ID) device to the patient and moving the patient into a healthcare facility that includes a robot face attached to a boom, the robot face receives a wireless signal from the wireless ID device and the remote station becomes coupled to the robot face.

8. The method of claim 7, further comprising coupling the portable face to a healthcare facility network through a wireless transceiver of the portable face.

9. A method for providing a remote medical consultation, comprising:
capturing an image of a physician with a station camera of a remote station, the remote station includes a station monitor, a station speaker and a station microphone;
transmitting the physician image to a portable face mounted to a platform, the portable face including a face monitor, a face camera, a face speaker and a face microphone;
displaying the physician image on the face monitor;
capturing an image of a patient with the face camera;
transmitting the patient image to the remote station;
displaying the patient image on the station monitor of the remote station;
transmitting an audio command from the station microphone to the face speaker;
moving the patient into a healthcare facility that includes a robot face attached to a boom; and,
coupling the robot face of the healthcare facility to the remote station, wherein the robot face of the healthcare facility receives a wireless signal from a wireless identification (ID) device associated with the patient.

10. A method for providing medical consultation, comprising:
capturing an image of a physician with a station camera of a remote station, the remote station includes a station monitor, a station speaker and a station microphone;
transmitting the physician image to a portable face, the portable face includes a face monitor, a face camera, a face speaker and a face microphone;
displaying the physician image on the face monitor;
capturing an image of a patient with the face camera;
transmitting the patient image to the remote station;
displaying the patient image on the station monitor of the remote station;
transmitting an audio command from the station microphone to the face speaker;
moving the patient into a vicinity of a robot that has a robot monitor, a robot camera, a robot speaker and a robot microphone; and,
coupling automatically the remote station to the robot, wherein the robot of the healthcare facility receives a wireless signal from a wireless identification (ID) device associated with the patient that causes the remote station to become coupled to the robot.

* * * * *